(12) United States Patent
Jiang et al.

(10) Patent No.: US 7,790,383 B2
(45) Date of Patent: Sep. 7, 2010

(54) GENETIC POLYMORPHISMS IN THE CORTICOTROPIN-RELEASING HORMONE (CRH) GENE AS MARKERS FOR IMPROVING BEEF MARBLING SCORE AND/OR SUBCUTANEOUS FAT DEPTH

(75) Inventors: Zhihua Jiang, Pullman, WA (US); Tito A. Wibowo, Pullman, WA (US); Jennifer J. Michal, Albion, WA (US)

(73) Assignee: Washington State University Research Foundation, Pullman, WA (US)

( * ) Notice: Subject to any disclaimer, the term of this patent is extended or adjusted under 35 U.S.C. 154(b) by 542 days.

(21) Appl. No.: 11/688,988

(22) Filed: Mar. 21, 2007

(65) Prior Publication Data

US 2007/0254296 A1 Nov. 1, 2007

Related U.S. Application Data

(60) Provisional application No. 60/784,360, filed on Mar. 21, 2006, provisional application No. 60/884,684, filed on Jan. 12, 2007.

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1
(58) Field of Classification Search ........................ None
See application file for complete search history.

(56) References Cited

OTHER PUBLICATIONS

Hacker U.T. et al. Gut (1997) vol. 40, No. 5, pp. 623-627.*
Juppner H. Functional properties of PTH/PTHrP receptor, Bone, Aug. 1995, vol. 17, No. 2, Supplement, pp. 39S-42S.
Thisted R.A. What is a P-value? May 25, 1998, University of Chicago ?Department of Statistics, available from www.stat.uchicago.edu/~thisted, pp. 1-6.
Wibowo T.A. et al. Corticotropin releasing hormone is a promising candidate gene for marbling and subcutaneous fat depth in beef cattle. Genome (2007) vol. 50, pp. 939-945.
Wibowo T.A. et al. Significant association of corticotrophin-releasing hormone gene with marbling and subcutaneous fat depth in Wagyu X Limousin Crosses. Plant & Animal Genomes XV Conference, Jan. 13-17, 2007. poster abstract P528: Cattle. From www.intl-pag.org, p. 1 of 1.
Barendse et al. A medium-density genetic linkage map of the bovine genome. Mamm Genome. Jan. 1997;8(1):21-8.
Casas et al. Quantitative trait loci affecting growth and carcass composition of cattle segregating alternate forms of myostatin. J Anim Sci. Mar. 2000;78(3):560-9.
Moore et al. Fine mapping of quantitative trait loci and assessment of positional candidate genes for backfat on bovine chromosome 14 in a commercial line of *Bos taurus*. J Anim Sci. Aug. 2003;81(8):1919-25.
Murani et al. Molecular characterization and evidencing of the porcine CRH gene as a functional-positional candidate for growth and body composition. Biochem Biophys Res Commun. Apr. 7, 2006;342(2):394-405.
Seasholtz et al. Corticotropin-releasing hormone-binding protein: biochemistry and function from fishes to mammals. J Endocrinol. Oct. 2002;175(1):89-97.
Stenzel-Poore et al. Development of Cushing's syndrome in corticotropin-releasing factor transgenic mice. Endocrinology. Jun. 1992;130(6):3378-86.

\* cited by examiner

*Primary Examiner*—Stephen Kapushoc
(74) *Attorney, Agent, or Firm*—Judy Jarecki-Black; Chad Kitchen; Merial Limited

(57) ABSTRACT

Aspects of the present invention also provide novel compositions and methods based on novel CRH single nucleotide polymorphisms selected from the group consisting of AAFC03076794.1:g.9657C>T, c.10718G>C, c.10841G>A, c.10893A>C and c.10936G>C, which may provide novel markers for marbling and/or subcutaneous fat depth. Additional aspects provide for novel methods which may comprise marker-assisted selection or marker-assisted management to improve marbling and/or subcutaneous fat depth in cattle.

2 Claims, 13 Drawing Sheets

```
CACGCGTCCGGGAAGAGAAGAGGAAAAGAACAGAGTGGGAAGAGAAAGGAGAAGGGAAGAGAACCGCTGA
AAAAAAAGCCCCAGAGACTTTCTCTGCAGAGAAGCGCTGCGCCCCGCTCACCTGCAGAAGCACCTCGGAA
GCGCCCGCTAAAATGCGACTGCGGCTGCTCGTGTCCGTGGGCGTCCTGCTGGTGGCTCTGCTGCCCTCCC
CGCCATGCAGGGCCCTCCTCAGCCGGGGGCCCATCCCGGGTGCCCGGCAGGCATCACAGCACCCCCAGCC
CCTGAGTTTCTTCCAGCCGCCGCCGCAGCCCCAGGAACCCCAGGCTCTGCCCACCCTACTCCGTGTTGGG
GAGGAATACTTCCTCCGCCTGGGTAACCTCGATGAGACCCGGGCTGCTCCGCTCTCTCCCGCCGCCTCGC
CTCTCGCCAGCAGAAGCAGCAGTCGCCTTTCTCCGGACAAGGTGGCCGCCAACTTTTTCCGAGCGCTGCT
GCAGCCCCGGCGCCCATTCGACAGCCCAGCGGGTCCCGCGGAACGCGGCACGGAGAACGCCCTCGGCAGC
CGCCAGGAGGCGCCGGCCGCCAGGAAGAGGCGATCCCAGGAACCTCCCATCTCCCTGGATCTCACCTTCC
ACCTCCTCCGAGAAGTCTTGGAAATGACCAAGGCCGATCAGTTAGCACAGCAAGCTCATAACAACAGGAA
ACTGTTGGACATTGCTGGGAAATGAAACGGTGCGTTTGGCTAAAA
```

FIG. 2A

```
CTTCCCCTTCTCTCCCCTCCCATTCACTCTCTTTTCTGACCTTCCCTTTGGCCTTTCCTAGTAAGAGGCCAGTAT
GTTTTCACACTTGGGAAATCTCATTCAAGAATTTTTGTCAATGGACAAGTCATAAGAAGCCCTTCCATTTTAGGG
CTCGTTGACGTCATCAAGGAGGCGATAAATATCTGTTGATATAATTGGATGTGAGATTCAGTGTTGAGATAGCAA
AAATTCTGCCCCTCGTTCCCGGGCAGGGCCCTATGATTTATGCAGGAGCAGAGGCAGCGGGCAATCCAGCTGTCA
AGAGAGCGTCAGCTTATTAGGCAAATGCTGCGTGGTTTCTGAAGAGGGTCGACACTATAAAATCCCCTTCCAGGC
TCTGGTGTGGAGAAACTCAGAGCCCACGTCCGTGGAGAGACAGAAGAGGAAGAGAAGAGGAAAAGAACAGAGTGG
GAAGAGAAAGGAGAAGGGAAGAGAACCGCTGAAAAAAAAGCCCCACAGACTTTCTCTGCAGAGAAGCGCTGCGCG
CCGCTCACCTGCAGAAGCACCTCGGAAGGTAGGGAGCGCCTAGACAGAACTGCGCCTCCAGCTTTGCACTGCCTG
AGCTGCCAGGGTGTGCGCAGCGCTGCCGGCTGTTCCTAGGCGTGTGTGTATATGTGTGTGTGTGTTTGTGTGTGA
ACGCGCGCGCGTGGGCGCGCGTTTGTGCGCGCCCGTGCCACAAGATTCCAATAGATAGTAGCTGAGATGCTACTA
AAAGCAAACTTAGACGGCTGCTCAGCGTTACCTGAACTGGCCGTTAATCCTCGCTGTGTAAACGAGCCCCCATCC
ATCCCGACCACCACCGAGAGAACCGAGGGCAGGGATGGGAAAAGAGGAAGGAGAGGCAGCAGTTCTGTTTGGAGG
AAAAGCTGAAACATCCGGAAAGGGTGGTGGTGGGGTCGCGGGGAGGGGGAATGTTTAGAGCCCTTGAGACCACG
AATTTGCAGGTCTTCTTTAGAGCCCGGGGAATTGATCTGGGGGAATCGTTAGACAGGGGACTCGGGGACCCTCCC
TAAGTGAGTCTTGTAAGGAGAGTCGCTCCAGCCTGGAGCGGGACTGAGCCTTGTTGCTGCGCCCTGCCCTTCCAA
GCTGCTCCCCTTGGTCTCACTCCATCTCTGGAAGTCCTAATTCGGGCGCTTCAGCACTACGGACAGCGCCCCACC
CGCGCCGGGAGCTGGGTCTGTGGGTGTCGTCCTGCGGGAAGACTCCCAGTGGAGCTCAACTCTGATAACTCTCTC
TTTTTTTCTCTCTCATTCCGCCCCCTGCCCACCTCTGTACCGCAATTAGCGGCCCGCTAAAATGCGACTGCGGCTG
CTCGTGTCCGTGGCCGTCCTGCTGGTGGCTTGCTGCCCTCCCCGCCATCGAGGCGCCTCCTCAGCCGCCGCCC
ATCCCGGGTGCCCGGCAGGCATCACAGCACCCCCAGCCCCTGACTTTCTTCCAGCCGCCGCCGCAGCCCAGGAA
GCCGAGGCTCTGCCCACCCGATCCGTGTTGGGGAGGAATACTTCCTCCGCCTGGGTAACCTCGATGAGACCCGG
GCTGCTCCGCTCTCTCCCGCCGGCCTCGCCCTCTCGCCAGCAGAAGCAGCAGTCGGCCTTTCTCCGGACAAGGTGGCC
GCCAACTTTTTCCCGAGCGCTGCTGCAGCCCCGGCGCCCATTCGACAGCCCAGCGGGTCCCGCCGGAACGCGGCACG
GAGAACGGCCTCGCCAGCCGCCAGGAGCGCCCCGGCTCGCCAGGAAGAGGCCGATCCCAGGAACCTCCCATCTCCCTG
GATCTCAGCCTTCCACCTCCTCCGAGAAGTCTTGGAAATGACCAAGGCCGATCAGTTAGCACAGCAAGCTCATAAC
AACAGGAAACTGTTGGACATTGCTGGGAAATGAAACGGTGCGTTTGGCTAAAAGATTCTGTATTTAGCACAAAA
GTGAATTTAAAAATCTAAAAATTGAAAAATAAAAATACAATATTCTATACCATAGCATTGCTCTGATACCATGTT
TATTTTTATATAGATTGAGATGTAGAGGATGTAC
```

FIG. 2B

```
- 409   CCCCTCCCATTCACTCTCTTTTCTGACCTTCCCTTTGGCCTTTCCTAGTAAGAGGCCAGT
- 349   ATGTTTTCACACTTGGGAAATCTCATTCAAGAATTTTTGTCAATGGACAAGTCATAAGAA
- 289   GCCCTTCCATTTTAGGGCTCGTTGACGTCATCAAGGAGGCGATAAATATCTGTTGATATA
- 229   ATTGGATGTGAGATTCAGTGTTGAGATAGCAAAAATTCTGCCCCTCGTTCCCGGGCAGGG
                 Neuron-restrictive silencer factor
                                   E2F
                              CDF-1
                               CP2
                                    C
- 169   CCCTATGATTTATGCAGGAGCAGAGGCAGCG GCAATCCAGCTGTCAAGAGAGCGTCAGC
                                    T

- 109   TTATTAGGCAAATGCTGCGTGGTTTCTGAAGAGGGTCGACACTATAAAATCCCCTTCCAG

Putative transcriptional start site +1
-  49   GCTCTGGTGTGGAGAAACTCAGAGCCCACGTCCGTGGAGAGACAGAAGAGGAAGAGAAGA
+  12   GGAAAAGAACAGAGTGGGAAGAGAAAGGAGAAGGGAAGAGAACCCGCTGAAAAAAAGCCC
+  72   CAGAGACTTTCTCTGCAGAGAAGCGCTGCGCCCCGGCTCACCTGCAGAAGCACCTCGGAAG
```

FIG. 2C

|         |                                                                      |
|---------|----------------------------------------------------------------------|
| CattleC | GGCAGGGCCCTATGATTTATGCAGGAGCAGAGGCAGCGCGCAATCCAGCTGTCAAGAGAGCGTCAG |
| CattleT | GGCAGGGCCCTATGATTTATGCAGGAGCAGAGGCAGCGTGCAATCCAGCTGTCAAGAGAGCGTCAG |
| Human   | GGCAGGGCCCTATGATTTATGCAGGAGCAGAGGCAGCACGCAATCGAGCTGTCAAGAGAGCGTCAG |
| Pan     | GGCAGGGCCCTATGATTTATGCAGGAGCAGAGGCAGCACGCAATCGAGCTGTCAAGAGAGCGTCAG |
| Pig     | GGCAGGGCCCTATGATTTATGCAGGAGCAGAGGCAGCACGCAATCGAGCTGTCAAGAGAGCGTCAG |
| Macaca  | GGCAGGGCCCTATGATTTATGCAGGAGCAGAGGCAGCACGCAATCGAGCTGTCAAGAGAGCGTCAG |
| Dog     | GGCAGGGCCCTATGATTTCTGCAGGAGCAGAGGCAGCACGCAATCGAGCTGTCAAGAGAGCGTCAG |
| Mouse   | GGCAGGGCCCTATTATTTATGCAGGAGCAGAGGCAGCACGCAATCGAGCTGTCAAGAGAGCGTCAG |
| Rat     | GGCAGGGCCCTATTATTTATGCAGGAGCAGAGGCAGCACGCAATCGAGCTGTCAAGAGAGCGTCAG |
| Sheep   | GGCAGG---CCTATGATTTATGCAGGAGCAGAGGCAGCG-GCAATCCAGCTGTCAAGAGAGCGTCAG |
| Consensus | GGCAGGgcCCTATgATTTATGCAGGAGCAGAGGCAGCgcGCAATCcAGCTGTCAAGAGAGCGTCAG |

Neuron Restrictive Silencing Element (NRSF)

GENETIC POLYMORPHISMS IN THE CORTICOTROPIN-RELEASING HORMONE (CRH) GENE AS MARKERS FOR IMPROVING BEEF MARBLING SCORE AND/OR SUBCUTANEOUS FAT DEPTH

INCORPORATION BY REFERENCE

This application claims benefit of U.S. provisional patent application Ser. No. 60/784,360 filed Mar. 21, 2006 and U.S. provisional patent application Ser. No. 60/884,684 filed Jan. 12, 2007.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

Aspects of the present invention relate generally to marbling and/or subcutaneous fat depth in beef cattle, and more particularly to novel compositions (e.g., markers) and methods for monitoring or predicting marbling and/or subcutaneous fat depth (SFD), for example, in beef cattle. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals with an advantage for an inheritable traits such as circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection.

Bovine chromosome 14 (BTA14) harbors several quantitative trait loci (QTL) that affect intramuscular fat (marbling) (see, e.g., Casas et al., J Anim Sci. 2000 March; 78(3):560-9) and subcutaneous fat depth (SFD) (see, e.g., Moore et al., J Anim Sci. 2003 August; 81(8):1919-25) in beef cattle. Recent studies have implicated the corticotrophin-releasing hormone (CRH) gene product in enabling mobilization of energy to cope with stress by stimulating hepatic gluconeogenesis, thus, influencing fat metabolism. Functional studies of the CRH gene in other species (including in mouse (see, e.g., Stenzel-Poore et al., Endocrinology. 1992 June; 130(6):3378-86) and swine (see, e.g., Seasholtz et al., J Endocrinol. 2002 October; 175(1):89-97) have suggested that CRH is highly associated with body composition (protein and lipid metabolism). The bovine CRH gene is located on BTA14 (see, e.g., Barendse et al., Mamm Genome. 1997 January; 8(1):21-8).

CRH is a growth inhibitor causing the release of glucocorticoids that in turn stimulate the production of both pro-opiomelancortin (POMC) and leptin, which are highly associated with obesity in mammals. Additionally, CRH is most known as a stress hormone. Stress stimulates hepatic gluconeogenesis that will influence fat and protein metabolism in peripheral tissue of animals. For example, a recent study on a porcine CRH gene showed that it functions as a major regulator of neuroendocrine response to stress. It mobilizes energy to cope with stress by stimulating hepatic gluconeogenesis and influencing fat metabolism. Therefore, CRH has a high impact in regulating energy homeostasis, and consequently, it affects body composition (fat deposition) and growth (see, e.g., Murani et al., Biochem Biophys Res Commun. 2006 Apr. 7; 342(2):394-405).

There is a pronounced need in the art for useful markers for intramuscular fat (marbling) (see, e.g., Casas et al., 2000, J Anim Sci. 2000 March; 78(3):560-9) and subcutaneous fat depth (SFD) (see, e.g., Moore et al., J Anim Sci. 2003 August; 81(8):1919-25) in beef cattle.

It remains advantageous to provide further SNPs that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

Aspects of the present invention provide genomic organization, single nucleotide polymorphisms and associations of the bovine CRH gene with beef marbling score (BMS) and subcutaneous fat depth (SFD) in Wagyu x Limousin $F_2$ crosses. Particular embodiments provide novel markers (e.g., the CRH gene) for marbling and/or subcutaneous fat depth in beef cattle. In silico techniques were used to determine the location of the CRH gene in bovine genome as well as both genomic and cDNA sequences of the bovine gene. Two pairs of primers were then designed to target the promoter, exon 1 and exon 2 regions of the gene. Sequencing of 6 F1 Wagyu X Limousin bulls revealed five single nucleotide polymorphisms in the gene. Genotyping these markers on ~250 $F_2$ progeny showed significant associations of the bovine CRH gene with the traits in beef cattle.

The present invention relates to the identification of genetic markers (single nucleotide polymorphisms (SNPs)) within the bovine gene encoding a bovine corticotropin-releasing hormone (CRH) and their associations with economically relevant traits in beef cattle production.

The invention encompasses a method for sub-grouping animals according to genotype wherein the animals of each sub-group have similar polymorphisms in a CRH gene which may comprise determining the genotype of each animal to be sub-grouped by determining the presence of SNP's in a CRH gene, and segregating individual animals into sub-groups wherein each animal in a sub-group has similar polymorphisms in a CRH gene.

The invention also encompasses a method for sub-grouping animals according to genotype wherein the animals of each sub-group have a similar genotype in CRH gene which may comprise determining the genotype of each animal to be sub-grouped by determining the presence of a single nucleotide polymorphism(s) of interest in CRH gene, and segregating individual animals into sub-groups depending on whether the animals have, or do not have, the single nucleotide polymorphism(s) of interest in CRH gene.

The genetic polymorphism(s) of interest may be selected from the group consisting of AAFC03076794.1:g.9657C>T, c.10718G>C, c.10841G>A, c.10893A>C and c.10936G>C.

The invention further relates to a method for sub-grouping animals according to genotype wherein the animals of each sub-group have a similar genotype in a CRH gene which may comprise determining the genotype of each animal to be sub-grouped by determining the presence of the above SNP, and segregating individual animals into sub-groups depending on whether the animals have, or do not have, the above SNP in a CRH gene.

The invention also relates to method for identifying an animal having a desirable phenotype as compared to the general population of animals of that species, which may comprise determining the presence of a single nucleotide polymorphism in a CRH gene of the animal, wherein the presence of the SNP is indicative of a desirable phenotype.

In an advantageous embodiment, the animal may be a bovine. In another advantageous embodiment, a CRH gene may be a bovine CRH gene.

The invention also encompasses computer-assisted methods and systems for improving the production efficiency for livestock having desirable marbling and/or subcutaneous fat depth and in particular the genotype of the animals as it relates to CRH SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within a CRH gene related to subcutaneous fat traits of the breed of animal and associating those data with other data about the animal or its herd, and maintaining those data in ways that are accessible. Another aspect of the invention encompasses a computer-assisted method for predicting which livestock animals possess a biological difference in marbling and/or subcutaneous fat depth, and which may include the steps of using a computer system, e.g., a programmed computer comprising a processor, a data storage system, an input device and an output device, the steps of: (a) inputting into the programmed computer through the input device data that includes a genotype of an animal as it relates to any one of the CRH SNPs described herein, (b) correlating marbling and/or subcutaneous fat depth predicted by the CRH genotype using the processor and the data storage system and (c) outputting to the output device the marbling and/or subcutaneous fat depth correlated to the CRH genotype, thereby predicting which livestock animals possess a particular marbling and/or subcutaneous fat depth.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a CRH genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2A shows the cDNA sequence of the bovine CRH gene (CO895988) (SEQ ID NO: 1). The coding sequence is underlined.

FIG. 2B shows the genomic DNA sequence of the bovine CRH gene derived from AAFC03076794.1 (SEQ ID NO:2). Primer sequences are underlined. Expressed sequences are highlighted and SNPs are bold and underlined.

FIG. 2C shows the nucleotide sequence (SEQ ID NO: 18) of the proximal promoter region of the bovine CRH gene. The putative transcription start site is numbered as +1. The polymorphic site is in bold and exon 1 is shaded. Potential transcription regulatory biding sites for NRSF, E2F, CDF-1 and CP2 are associated with allele C only.

FIG. 2D shows the sequence alignment of the partial CRH proximal promoter region among nine species with a conserved binding site for NRSF (boxed). The polymorphic site in the promoter of bovine CRH was detected (see arrow) with the allele T eliminating the conserved binding site. The sequences are from top to bottom, SEQ ID NOS: 3-13.

FIG. 3A represents GGAG, CGCG and CGCC, FIG. 3B represents CACG and FIG. 3C represents GAAG haplotype. The arrow shows the slightly different structure discovered between CACG and GAAG haplotypes.

FIG. 4A haplotypes between c.10718G>C and c.10936G>C, FIG. 4B haplotypes between g.9657C>T and c.10718G>C and FIG. 4C haplotypes between g.9657C>T and c.10936G>C. Different superscripts show significant differences (P values<0.05) between the two compared haplotypes.

DETAILED DESCRIPTION

Figure 1:
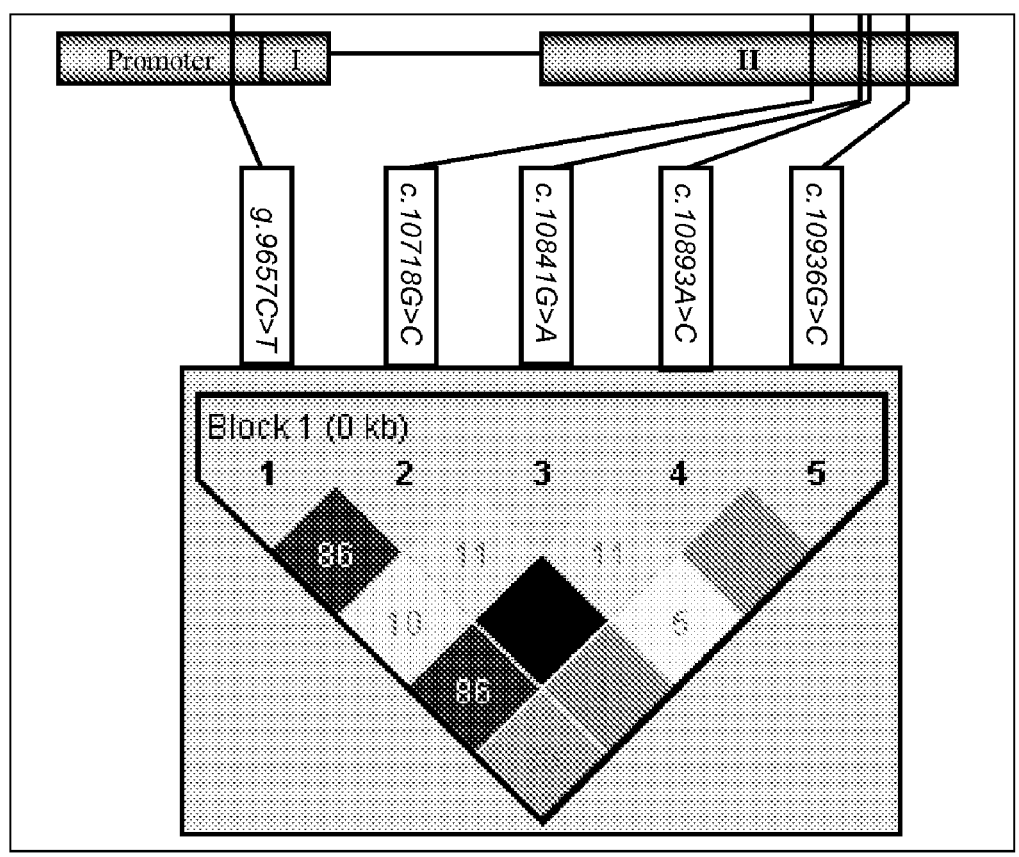
FIG. 1 illustrates genomic organization and haplotype analysis of the bovine CRH gene. The promoter region and exons (I and II) are shown as bars and the straight line represents an intron. Pairwise linkage disequilibrium relationship for 5 mutations (AAFC03076794.1:g.9657C>T, c.10718G>C, c10841 G>A, c. 10893 A>C and c.10936G>C) is illustrated based on $r^2$ measurements.

Bovine chromosome 14 (BTA14) harbors quantitative trait loci (QTL) that affect milk fat percentage and yield in dairy cattle (see, e.g., Viitala et al., J Dairy Sci. 2003 May; 86(5): 1828-36), and intramuscular fat (marbling) (see, e.g., Casas et al., 2000. J Anim Sci. 2000 March; 78(3):560-9) and subcutaneous fat depth (SFD) in beef cattle (see, e.g., Moore et al., J Anim Sci. 2003 August; 81(8):1919-25). The bovine CRH gene has been previously placed on BTA14 (see, e.g., Barendse et al., Mamm Genome. 1997 January; 8(1):21-8).

Corticotropin-releasing hormone (CRH) is a growth inhibitor causing the release of glucocorticoids that in turn stimulate the production of both pro-opiomelancortin (POMC) and leptin, which are highly associated with obesity in mammals. Additionally, CRH is most known as a stress hormone. Stress stimulates hepatic gluconeogenesis that will influence fat and protein metabolism in peripheral tissue of animals. For example, a recent study on a porcine corticotrophin-releasing hormone (CRH) gene showed that it functions as a major regulator of neuroendocrine response to stress. It mobilizes energy to cope with stress by stimulating hepatic gluconeogenesis and influencing fat metabolism. Therefore, CRH has a high impact in regulating energy homeostasis, and consequently, it affects body composition (fat deposition) and growth (see, e.g., Murani et al., Biochem Biophys Res Commun. 2006 Apr. 7; 342(2):394-405).

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as beef marbling, subcutaneous fat, meat yield, breeding yield, dairy form, meat quality and yield, daughter pregnancy rate (i.e., fertility), productive life (i.e., longevity) and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine CRH, the bovine CRH nucleotide sequence can be selected from, but is not limited to, the sequence corresponding to GenBank Accession No. AAFC03076794.1, bovine chromosome 14 (BTA14) or a fragment thereof or a region of the bovine genome that comprises this sequence.

The present invention, therefore, provides isolated nucleic acids that may specifically hybridize to the nucleotide sequence can be selected from, but is not limited to, the sequence corresponding to GenBank Accession No. AAFC03076794.1 or the complement thereof, and which comprises the polymorphic sites corresponding to the CRH SNPs.

The single nucleotide polymorphism(s) of interest may be selected from the group consisting of AAFC03076794.1: g.9657C>T, c.10718G>C, c.10841G>A, c.10893A>C and c.10936G>C.

The SNP advantageous in the present invention is associated with certain economically valuable and heritable traits relating to marbling and/or subcutaneous fat depth in bovines. Therefore, it is an object of the present invention to determine the genotype of a given animal of interest as defined by the CRH locus SNP according to the present invention. It is also contemplated that the genotype of the animal(s) may be defined by additional SNPs within the CRH gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly SNPs of the CRH gene. The methods further allow, by computer-assisted methods of the invention, to correlate the SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the CRH gene, advantageously of the region encompassing a CRH SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a CRH gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref} - N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a CRH gene which are unique to a CRH gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e. g., $^3$H, $^{125}$I, $^{35}$S, $^{14}$C, $^{32}$P, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^{3}H$, $^{125}I$, $^{35}S$, $^{14}C$, $^{32}P$, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and MacBeath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as marbling and/or subcutaneous fat depth. Continuous selection and breeding of animals, such as livestock, that are at least heterozygous and advantageously homozygous for desirable alleles of the CRH gene polymorphic sites associated with economically relevant traits of growth, feed intake, efficiency and/or carcass merit, and reproduction and longevity would lead to a breed, line, or population having higher numbers of offspring with economically relevant traits of growth, feed intake, efficiency and carcass merit, and reproduction and longevity. Thus, the CRH SNPs of the present invention can be used as a selection tool.

Desirable phenotypes include, but are not limited to, feed intake, growth rate, body weight, carcass merit and composition, and reproduction and longevity, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF%, %), marbling score (MBS, 10 to 99), marbling score divided by days on feed (MBS/DOF), quality grade, less than or equal to select versus greater than or equal to choice (QG,<Se vs,>Ch), ribeye area (REA, in$^2$), ribeye area per hundred weight HCW (REA/cwt HCW, in$^2$/ 100 lb hot carcass weight (HCW) and marbling and/or subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the CRH gene of the present invention. Other SNPs that may be included in panels of SNPs include, but not limited to, SNPs found in the CAST gene, diacylglycerol O-acyltransferase (DGAT1) gene, DOPEY2 gene, GHR gene, FABP4 gene, ghrelin gene, KIAA1462 gene, leptin (LEP) gene, NPY gene, ob gene, TFAM gene, and/or the UCP3 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as marbling and/or subcutaneous fat depth. The present invention provides methods of screening livestock to determine those more likely to develop a desired body condition by identifying the presence or absence of one or more gene polymorphisms correlated with marbling and/or subcutaneous fat depth.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin testing, bovine spongiform encephalopathy (BSE) diagnosis, brucellosis vaccination, FMD (foot and mouth disease) vaccination, BVD (bovine viral diarrhea) vaccination, Sure Health pre-conditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are CRH sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the CRH sequences described herein.

Another embodiment of the invention is an oligonucleotide that specifically hybridizes under high stringency conditions to any one of the polymorphic sites of the CRH gene, wherein the oligonucleotide is between about 18 nucleotides and about 50 nucleotides.

In another embodiment of the invention, the oligonucleotide comprises a central nucleotide specifically hybridizing with a CRH gene polymorphic site of the portion of the nucleic acid molecule.

Another aspect of the invention is a method of identifying a CRH polymorphism in a nucleic acid sample comprising isolating a nucleic acid molecule encoding CRH or a fragment thereof and determining the nucleotide at the polymorphic site.

Another aspect of the invention is a method of screening cattle to determine those bovines more likely to exhibit a biological difference in marbling and/or subcutaneous fat depth comprising the steps of obtaining a sample of genetic material from a bovine; and assaying for the presence of a genotype in the bovine which is associated with marbling and/or subcutaneous fat depth, the genotype characterized by a polymorphism in the bovine CRH gene.

In other embodiments of this aspect of the invention, the step of assaying is selected from the group consisting of: restriction fragment length polymorphism (RFLP) analysis, minisequencing, MALDI-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the CRH gene or a portion thereof that contains the polymorphism. In other embodiments of the invention, the amplification may include the step of selecting a forward and a reverse sequence primer capable of amplifying a region of the CRH gene.

Another aspect of the invention is a computer-assisted method for predicting which livestock animals possess a biological difference in marbling and/or subcutaneous fat depth comprising: using a computer system, e.g., a programmed computer comprising a processor, a data storage system, an input device and an output device, the steps of: (a) inputting into the programmed computer through the input device data comprising a CRH genotype of an animal, (b) correlating marbling and/or subcutaneous fat depth predicted by the CRH genotype using the processor and the data storage system and (c) outputting to the output device the marbling and/or subcutaneous fat depth correlated to the CRH genotype, thereby predicting which livestock animals possess a particular marbling and/or subcutaneous fat depth.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

The corticotropin releasing hormone (CRH) gene is mapped on bovine chromosome 14 (BTA14), where more than 30 fat-related quantitative trait loci (QTL) have been reported in dairy and beef cattle. The gene regulates secretion of adrenocortocotrophin hormone, the hypothalamic-pituitary-adrenal axis and multiple hypothalamic functions, therefore, we hypothesize that CRH is a strong candidate gene for beef marbling score (BMS) and subcutaneous fat depth (SFD) in a Wagyu x Limousin $F_2$ population. Two pairs of primers were designed and a total of five single nucleotide polymorphisms (SNPs) were identified, including AAFC03076794.1:g.9657C>T, c.10718G>C, c.10841G>A, c.10893A>C and c.10936G>C. Among these cSNPs, c.10718G>C, c.10841G>A, and c.10936G>C are missense mutations, leading to amino acid changes from arginine to proline, from serine to asparagine and from aspartic acid to histidine, respectively. These five SNPs were genotyped on ~250 $F_2$ progeny, but four were selected as tagging SNPs for association analysis due to no historical recombination observed between c.10718G>C and c.10893A>C. Statistical analysis showed g.9657C>T, c.10718G>C and c.10936G>C as well as their haplotypes had significant effects on SFD, but only c.10936G>C was significantly associated with BMS. The g.9657C>T in the promoter led to a gain/loss of a CpG site and four regulatory binding sites. Different haplotypes among four cSNP had significant impact on the mRNA secondary structures, but no associations with phenotypes. Overall, our results provide further evidence that CRH is a strong candidate gene for a concordant QTL related to lipid metabolism in mammals.

Genome wide screenings using microsatellite markers have shown that bovine chromosome 14 (BTA14) harbors quantitative trait loci (QTL) for both beef marbling score (BMS) and subcutaneous fat depth (SFD) in beef cattle. In two half-sib families developed by mating a Belgian Blue x MARC III sire and a Piedmontese x Angus sire to MARC III dams, Casas and colleagues (see, e.g., Casas et al., 2000, J Anim Sci. 78: 560-569) observed a QTL for fat depth at 38 cM that interacted with myostatin genotypes on BTA2. In a half-sib family produced by mating a Brahman x Hereford sire to Hereford, Angus, Hereford x Augus and MARCIII dams, the same group identified a fat-depth QTL at 16 cM, and a marbling QTL at 47 cM on BTA14 (see, e.g., Casas et al., 2003, J Anim Sci. 78: 560-569). A QTL for marbling on BTA14 was also detected in a half-sib family of 348 purebred Japanese Wagyu steers, but it is located at 53 cM (see, e.g., Mizoshita et al., 2004, J Anim Sci. 82: 3415-3420).

Both diacylglycerol O-acyltransferase 1 (DGAT1) and thyroglobulin (TG) have been proposed as potential candidate genes for marbling and fat depth QTLs on BTA14, because they affect lipid metabolism. The DGAT1 enzyme utilizes diacylglycerol and fatty acyl CoA as substrates in order to catalyze the final stage of triacylglycerol synthesis, while thyroglobulin is the glycoprotein precursor to the thyroid hormones whose metabolism is important for energy expenditure and dissipation of heat in tissues. However, associations of these two genes with both marbling and fat depth have been reported inconsistently among different populations. In a Canadian beef population, neither DGAT1 nor TG showed a significant ($P>0.10$) association with the backfat EBV (estimated breeding value) (see, e.g., Moore et al., 2003, J Anim Sci. 81: 1919-1925). In a study using 22 Brahman sire families mated to the Brahman dams, Casas and colleagues (see, e.g., Casas et al., 2005, J Anim Sci. 83: 13-19) reported a significant association of TG with fat thickness ($P<0.05$), but not with marbling score. No significant associations of the DGAT1 polymorphism were observed for either marbling or fat thickness. Just recently, a meta-analysis conducted on an Australian beef population provided substantial evidence for an additive association between a TG marker and marbling using a Bayesian hierarchical model (see, e.g., Wood et al., 2006, Genet Sel Evol. 38: 479-494). All these data indicate that genes underlying QTLs for both marbling and fat depth on BTA14 remain unclear.

Corticotrophin releasing hormone (CRH) is involved in many biological and physiological actions and functions. Basically, CRH plays an important role as the major hypothalamic releasing factor for pituitary adrenocorticotropin (ACTH) secretion (see, e.g., Seasholtz et al., 2002, J Endocrinol. 175: 89-97), which regulates glucocorticoid and catecolamines to mediate stress response. Behavioral effects of CRH include increased locomotor activity and inhibition of food intake, while its actions on metabolism are mediated mainly by activation of the sympathetic nervous system (see, e.g., Rothwell, 1990, Neurosci Biobehav Rev. 14: 263-271). Interestingly, there is increasing evidence supporting the involvement of this CRH peptide in the regulation of energy balance and body weight, influencing both food intake and sympathetically-mediated thermogenesis. For example, the increased activity of the hypothalamic-pituitary-adrenal (HPA) axis stimulated by CRH is highly associated with abdominal fat (see, e.g., Perusse et al., 2001, Diabetes, 50: 614-621). Furthermore, ACTH secretion under a stress environment stimulates glucocorticoids, which help return the stress system to homeostasis and mediate many metabolic changes, such as increases of leptin production (see, e.g., Seasholtz et al., 2002, J Endocrinol. 175: 89-97; Buchanan et al., 2005, Anim Genet. 36: 127-131). As the CRH gene is located on bovine chromosome 14 (BTA14), Applicants decided to validate its candidacy for marbling and SFD in a Wagyu x Limousin $F_2$ cross.

Animals. A Wagyu x Limousin reference population was generated jointly by Washington State University and the Fort Keogh Livestock and Range Research Laboratory, ARS, USDA, as described previously (see, e.g., Jiang et al., 2005, Biochem Biophys Res Commun. 334: 516-523). However, DNA extraction on 6 $F_1$ bulls, 113 $F_1$ dams and ~250 $F_2$ progeny plus performance data collection on these $F_2$ animals was conducted in the USDA laboratory. Beef marbling score (BMS) was a subjective measure of the amount of intramuscular fat in the longissimus muscle based on USDA standards See USDA Agricultural Marketing Service website), ranging from $4=\text{Slight}^0$ to $9.5=\text{Moderately Abundant}^{50}$ (SD=1.00) in this $F_2$ population. Subcutaneous fat depth (SFD) was measured at the $12-13^{th}$ rib interface perpendicular to the outside surface at a point three-fourths the length of the longissimus muscle from its chine bone end with a range of 0.1 to 1.3 inches (SD=0.18) in this $F_2$ population.

DNA sequences and primer design. The cDNA sequence (CO895988, SEQ ID NO: 1) and genomic DNA contig (AAFC03076794, SEQ ID NO: 2) of the bovine CRH gene were retrieved from GenBank databases and were used to determine genomic organization by sequence alignment. Primer design was completed using the online oligonucleotide design tool Primer3. Two pairs of primers were designed: one targeted the proximal promoter and exon 1 (forward—5'CCC CTC CCA TTC ACT CTC TTT TCT 3' (SEQ ID NO: 14) and reverse—5'AGT TCT GTC TAG GCG CTC CCT ACC3' (SEQ ID NO: 15)), and the other amplified exon 2 region (forward—5' GGG TCT GTG GGT GTC GTC CT 3' (SEQ ID NO: 16) and reverse—5' AAA AAT AAA CAT GGT ATC AGA GCA ATG 3' (SEQ ID NO: 17)) of the bovine CRH gene, respectively.

Mutation detection and genotyping. Approximately 50 ng of genomic DNA each from six Wagyu x Limousin $F_1$ bulls was amplified in a final volume of 10 μL that contained 12.5 ng of each primer, 150 μM dNTPs, 1.5 mM $MgCl_2$, 50 mM KCl, 20 mM Tris-HCl and 0.25U of Platinum Taq polymerase (Invitrogen, Carlsbad, Calif.). The PCR conditions were carried out as follows: 94° C. for 2 min, 35 cycles of 94° C. for 30 sec, 60° C. for 30 sec and 72° C. for 30 sec, followed by a further 5 min extension at 72° C. PCR products were then sequenced on ABI 3730 sequencer in the Laboratory for Biotechnology and Bioanalysis (Washington State University) using a standard protocol and polymorphisms detected. A single nucleotide polymorphism (SNP) was detected in the promoter/exon 1 product, which could be revealed by digestion with restriction enzyme HhaI. Four SNPs were identified in the exon 2 region and genotypes of the $F_2$ progeny were performed using a PCR product direct sequencing.

Data analysis. The degrees of Hardy-Weinberg equilibrium within each marker and linkage disequilibrium among different markers in the bovine CRH gene were estimated using the HAPLOVIEW program (see, e.g., Barrett et al., 2005, Bioinformatics, 21: 263-265). The phenotypic data for both BMS and SFD measurements were previously adjusted for year of birth, sex, age (days), live weight (kilograms), or fat depth (inches), as appropriate. The adjusted phenotypes were then used in a subsequent association analysis using the GLM (general linear model) procedure of SAS v9.1 (SAS institute Inc., Gary, N.C.). Pair-wise comparisons of least squares means were performed using a protected t-test. Additionally, quantitative transmission disequilibrium test (QTDT) (see, e.g., Abecasis et al., 2000, Am J Hum Genet. 66: 279-292) was performed to further examine the association between markers and adjusted obesity-related phenotype data. P value <0.05 was considered statistically significant. The MatInspector web server (see, e.g., Quandt et al., 1995, Nucleic Acids Res. 23: 4878-48) was used to screen potential transcriptional regulatory binding site changes caused by promoter polymorphisms, while the Mfold web server (see, e.g., Zuker, 2003, Nucleic Acids Res. 31: 3406-3415) was used to predict mRNA secondary structure changes caused by coding polymorphisms.

Annotation of the bovine CRH gene. A GenBank database search surprisingly revealed that the bovine CRH gene has not been well annotated. Although a sequence (AF340152, see, e.g., Buchanan et al., Anim Genet. 2005 April; 36(2):127-31) with a complete coding sequence for the bovine gene was submitted to the GenBank in 2001, it represents the exon 2 region only. In the present Example, therefore, Applicants did a BLAST search against the bovine EST (expressed sequence tags) database using the sequence AF340152 as a reference and retrieved a full-length cDNA sequence (CO895988, SEQ ID NO: 1) for the bovine CRH gene. A genomic DNA contig (AAFC03076794, SEQ ID NO: 2) for the same gene was then retrieved from the bovine genome sequence database and thus alignment between the cDNA sequence and the genomic sequence determined the genomic organization of bovine CRH gene (FIG. 1 and FIGS. 2A and 2B). Like its human ortholog, the bovine CRH gene has two exons and one intron. Exon 1 is a non-coding exon, but exon 2 contains 11 bp of non-coding sequence and 573 bp of complete coding sequence. The size of intron 1 is 771 bp in length (AAFC03076794). In addition, five ESTs (EE338630, DV826091, DV825584, DV822182, and EE339662) show that the bovine CRH gene might encode a new splicing form with a prohormone of 130 amino acids, 60 amino acids shorter than the regular one. So far, no new splicing forms of CRH gene have been reported in other mammals.

SNPs and haplotypes. A total of five single nucleotide polymorphisms were identified, including one SNP (AAFC03076794.1:g.9657C>T) in the proximal promoter region and four coding SNPs (AAFC03076794.1: c.10718G>C, c.10841G>A, c.10893A>C and c.10936G>C) in the exon 2 region (FIG. 2B). Among these four cSNPs, three (c.10718G>C, c.10841G>A, and c.10936G>C) are missense mutations, leading to amino acid changes from arginine to proline, from serine to asparagine and from aspartic acid to histidine, respectively. The minor alleles among these five SNPs are C, G, A, A, C respectively, with a frequency ranging from 0.08 to 0.42. Genotyping on ~250 $F_2$ progeny indicated that all five SNPs fall into the Hardy-Weinberg equilibrium (P>0.05). HAPLOVIEW analysis indicated that among these five SNPs, two SNPs c.10718G>C and c.10893A>C have no-historical recombination by forming two haplotypes of CC and GA (FIG. 1), and thus eight haplotypes were identified in the population, including TCGCC, CGGAG, TCGCG, CGAAG, CCGCC, TGGAG, TGAAG and CCACG with a frequency of 0.368, 0.326, 0.204, 0.070, 0.016, 0.012, 0.003 and 0.002, respectively.

Promoter SNP and potential regulatory binding sites. Screening the proximal promoter region using MatInspector web server program revealed that allele g.9657C, but not g.9657T gains four possible transcription factor binding sites, including neuron restrictive silencer factor (NRSF), E2F transcription factor, CDE-CHR binding factor-1 (CDF-1) and transcription factor CP2 (FIG. 2C). In fact, the promoter region flanking the polymorphic site in cattle is highly conserved in other mammals, such as human (NT_008183.18), chimpanzee (XM_519792.2), rhesus monkey (XM_001094433.1), mouse (NW_001030719.1), rat (M54987.1), sheep (M22853.1), dog (AB162117) and pig (DQ358705.1) (FIG. 2L). However, among the four regulatory binding sites gained by the allele g.9657C in cattle, only the NRSF is retained in all of other eight species (FIG. 2D).

Figure 3A:
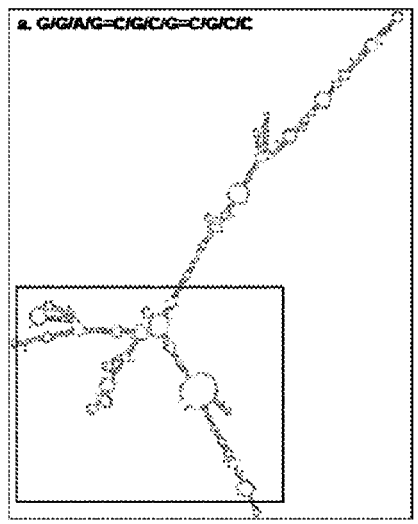
FIGS. 3A-3C illustrates predicted mRNA secondary structure of bovine CRH gene based on five haplotypes.
Figure 3B:
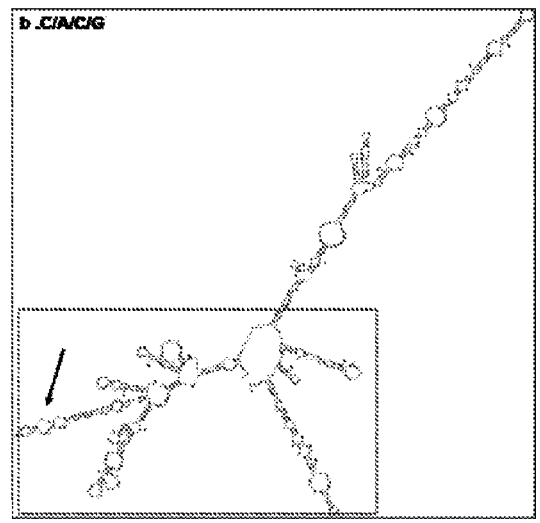
Figure 3C:
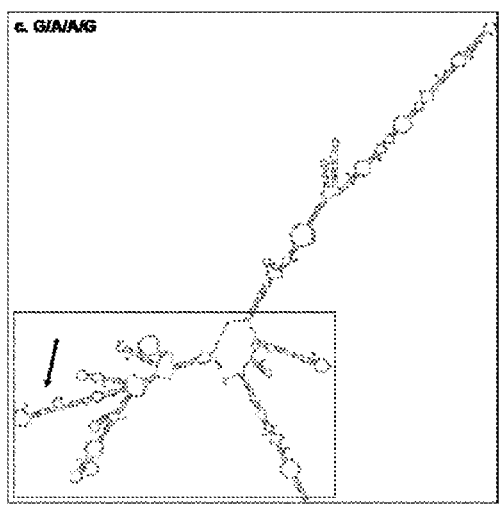

Coding SNPs and the mRNA secondary structure. HAPLOVIEW analysis indicated that four cSNP (c.10718G>C, c.10841G>A, c.10893A>C and c.10936G>C) form five haplotypes: GGAG, CGCG, CGCC, CACG and GAAG, respectively. The Mfold program (see, e.g., Zuker, 2003, Nucleic Acids Res. 31: 3406-3415) was used to predict how these haplotypes affect mRNA secondary structure involving a complete coding sequence of 573 bp for the preprohormone of the bovine CRH gene. FIG. 3A shows that the first three haplotypes (GGAG, CGCG and CGCC) gave the same secondary structures. The secondary structures of the last two haplotypes are illustrated in FIGS. 3B and 3C, respectively, but they just slightly differ from each other (see arrows inside the boxes). However, there was a remarkable difference in the secondary structure between the first three haplotypes and the last two haplotypes. Obviously, polymorphic site c.10841G>A plays a critical role in determining the secondary structure of the CRH mRNA in cattle.

Association analysis of SNPs with SFD and marbling. As both SNPs—c.10718G>C and c.10893A>C have no-historical recombination events in the population, four tagging SNPs—g.9657C>T, c.10718G>C, c.10841G>A and c.10936G>C were used in the association analysis. Except the SNP c.10841G>A, all other three SNPs were significantly associated with SFD (Table 1). The difference in SFD between two homozygotes reached 0.12 inches at g.9657C>T (P<0.01), 0.10 inches at c.10718G>C (P<0.001) and 0.11 inches at c.10936G>C (P<0.005), respectively, which account for 0.56-0.67 standard deviation of the trait in the population. However, only one SNP c.10936G>C had a significant effect on BMS (Table 1). Animals with CC genotypes had marbling scores that were 0.549 (P<0.05) and 0.399 (P<0.05) lower than animals with GG and CG genotypes, which account for 0.549 and 0.399 standard deviations for the trait, respectively.

TABLE 1

Association analysis of the bovine CRH gene with SFD and BMS in Wagyu × Limousin F2 crosses.

| | | | SFD (in inches) | | | BMS (in inches) | | |
|---|---|---|---|---|---|---|---|---|
| Marker | Genotype | #Animals | LSM ± S.E. | $P_{GLM}$ | $P_{QTDT}$ | LSM ± S.E. | $P_{GLM}$ | $P_{QTDT}$ |
| g.9657C>T | CC | 43 | 0.485 ± 0.024[a] | 0.001 | 0.0002 | 6.010 ± 0.147[a] | 0.669 | 0.026 |
| | CT | 107 | 0.396 ± 0.015[b] | | | 5.882 ± 0.093[a] | | |
| | TT | 82 | 0.365 ± 0.017[b] | | | 5.809 ± 0.106[a] | | |
| c.10718G>C | CC | 84 | 0.357 ± 0.017[a] | 0.002 | 0.0004 | 5.791 ± 0.106[a] | 0.477 | 0.254 |
| | CG | 111 | 0.403 ± 0.015[b] | | | 5.939 ± 0.092[a] | | |
| | GG | 43 | 0.458 ± 0.024[c] | | | 5.973 ± 0.148[a] | | |

TABLE 1-continued

Association analysis of the bovine CRH gene with
SFD and BMS in Wagyu × Limousin F2 crosses.

| Marker | Genotype | #Animals | SFD (in inches) | | | BMS (in inches) | | |
| --- | --- | --- | --- | --- | --- | --- | --- | --- |
| | | | LSM ± S.E. | $P_{GLM}$ | $P_{QTDT}$ | LSM ± S.E. | $P_{GLM}$ | $P_{QTDT}$ |
| c.10841G>A | AG | 36 | $0.441 \pm 0.026^a$ | 0.067 | 0.0653 | $5.921 \pm 0.160^a$ | 0.847 | 0.846 |
| | GG | 204 | $0.388 \pm 0.011^a$ | | | $5.887 \pm 0.068^a$ | | |
| c.10936G>C | CC | 33 | $0.333 \pm 0.028^a$ | 0.002 | 0.0005 | $5.493 \pm 0.168^a$ | 0.022 | 0.009 |
| | CG | 118 | $0.383 \pm 0.014^a$ | | | $5.892 \pm 0.088^b$ | | |
| | GG | 88 | $0.438 \pm 0.017^b$ | | | $6.042 \pm 0.103^b$ | | |

* Means within a column with different superscripts are significantly different (P < 0.01)

Figures 4A, 4B, 4C:
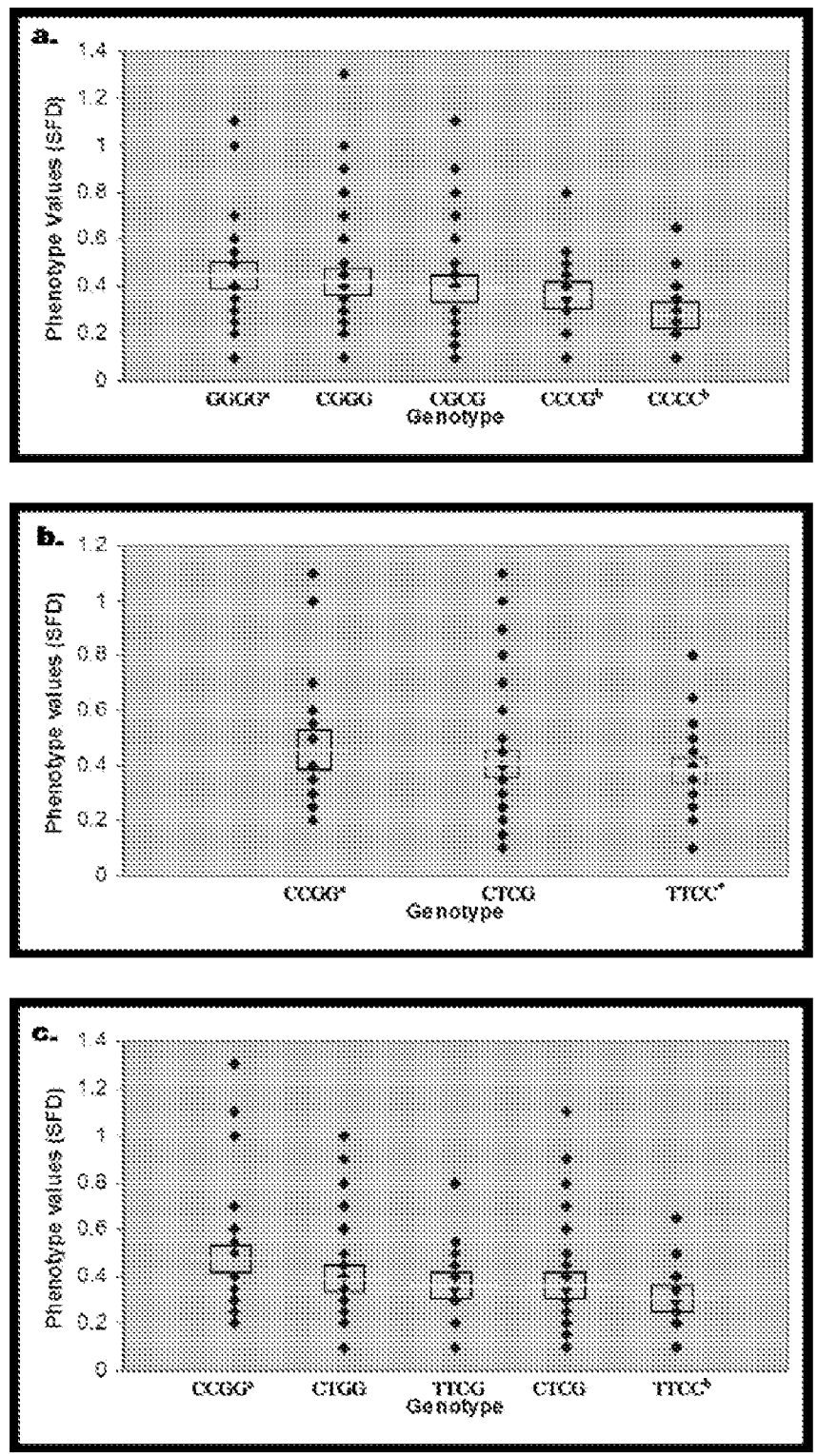
FIGS. 4A-4C shows the association plot of haplotypes with SFD values (in inches).

Association analysis of haplotypes with SFD. As indicated above, three SNPs g.9657C>T, c.10718G>C, and c.10936G>C were associated with SFD in the reference population. Therefore, Applicants decided to determine how their haplotypes affect the trait, but any haplotype with five or less animals was excluded in the analysis. FIG. 4A shows an association plot of haplotypes between c.10718G>C and c.10936G>C with SFD measurements in inches. The SFD of haplotype GGGG was 0.146 inches (P<0.05) greater than its CCCC counterpart. For the haplotypes between g.9657C>T with c.10718G>C (FIG. 4B), animals with CCGG had SFD that was 0.102 inches (P<0.05) greater than animals with TTCC haplotype. FIG. 4C shows an association plot of haplotypes between g.9657C>T and c.10936G>C. The same trend was observed with a difference of 0.177 inches between CCGG and TTCC haplotypes.

Corticotrophin releasing hormone (CRH) released from the hypothalamus to the anterior pituitary under stress condition stimulates secretion of adrenocorticotrophic hormone (ACTH), which up-regulates the cortisol level. Cortisol has profound metabolic effects, such as stimulating gluconeogenesis (in the liver), inhibiting glucose uptake (in muscle and adipose tissue) and stimulating fat breakdown (in adipose tissue). Hence, research on CRH has broadened not only to stress-related studies but also to any metabolic diseases. Transgenic mice that over-express CRH exhibit hair loss, muscle wasting, decreased linear growth and obesity (see, e.g., Stenzel-Poore et al., 1992, Endocrinology, 130: 3378-3386). These conditions were also observed in man and other animals with Cushing syndrome disease, which is also caused by an increase in endogenous cortisol, with metabolic aberration, muscle wasting and obesity as some of the clinical symptoms. Furthermore, SNPs in the porcine CRH gene were significantly associated with back fat thickness, carcass length, average daily gain and longissimus muscle area (see, e.g., Murani et al., 2006, Biochem Biophys Res Commun. 342: 394-405). In a Charolais-cross steer population, Buchanan and colleagues (see, e.g., Buchanan et al., 2005, Anim Genet. 36: 127-131) reported that three SNPs in the bovine CRH gene were highly associated with end-of-test rib eye area (P<0.034) and hot carcass weight (P<0.0015). In the present Example, Applicants demonstrated that the bovine CRH gene was significantly associated with marbling and SFD in a Wagyu x Limousin $F_2$ population. All these data indicate that CRH is a strong candidate gene for concordant QTLs related to body composition and energy metabolism.

In the present Example, a SNP in the promoter region of the bovine CRH gene caused a transition of cytosine to thymine (g.9657C>T). This mutation is located 138 bases from the putative transcriptional start site and forms a CpG site when allele C occurs (FIG. 2C). If this CpG site is methylated, transcriptional activity could be severely suppressed by inhibition of a sequence-specific transcription factor binding region because of the alteration by the methylated cytosine in the recognition sites, blockage by some CpG binding protein (such as MeCP-1 and MeCP2) and alteration of chromatin structures (see, e.g., Kudo and Fukuda, 1995, J Biol Chem. 270: 13298-13302). On the other hand, the MatInspector program revealed that allele 9657T eliminates four potential regulatory binding sites: neuron restrictive silencer factor (NRSF), E2F transcription factor, CDE-CHR binding factor-1 (CDF-1) and transcription factor CP2 (FIG. 2C). Cross species alignment (FIG. 2D) indicated that the proximal promoter region flanking the polymorphic site is highly conserved in nine mammalian species, suggesting evolutionary importance of the region in the transcription regulatory sites of CRH. Moreover, MatInspector analysis revealed that among the four binding sites described above, only NRSF is conserved among species. Seth et al. (see, e.g., Seth et al., 2001, J Biol Chem. 276: 13917-13923) showed that NRSF was found in the first intronic region of CRH and it represses the gene expression through a HDAC-dependent mechanism. However, NRSF also acts as an enhancer of transcription activity. When a RE-1/NRSE region is either disrupted or deleted from the intronic region of CRH, a significant 1.2-2.5 fold up regulation in reporter activity was observed (see, e.g., Seth et al., 2001, J Biol Chem. 276: 13917-13923).

However, Applicants cannot exclude the involvement of the three other regulatory elements in regulating of CRH expression in cattle. E2F is a heterodimeric protein that plays an important role in cell growth and apoptosis. Study in the methylated promoter region of genes that are regulated by E2F, such as in dhfr, E2F1, cdc2, c-myb and c-myc, showed that methylation can block the E2F elements (see, e.g., Campanero et al., 2000, Proc Natl Acad Sci U S A. 97: 6481-6486). Furthermore, a previous study also showed that methylation of the first cytosine residue in the GCGC motif of the E2F element, which is the case of the bovine CRH polymorphic site (FIG. 2C), blocks the binding of E2F protein from the cell extract and interferes with transcription activity of the gene. CDF-1 is a stereospecific transcription regulatory factor that recognizes two binding sites (CDE and CHR region). Inverting the position of CHR and CDE region abolishes the cell-cycle regulated repression, without affecting transcription, suggests that CDF-1 interacts with the activating domain to mediate repression (see, e.g., Zwicker et al., 1997, Nucleic Acids Res. 25: 4926-4932). The functional role of CP-2 transcription factor was still unclear due to its ability to not only act as a ubiquitous transcription factor to most tissues but it can also be involved in tissue or stage specific transcription of some genes (see, e.g., Kang et al., 2005, FEBS J. 272: 1265-1277). Nevertheless, the promoter polymorphism (g.9657C>T) leaves us many physiological and functional questions to answer in the future.

Four SNPs (c.10718G>C, c.10841G>A, c.10893A>C and c.10936G>C) were also detected in the exon 2 coding region of the bovine CRH gene. One mutation (c.10893A>results in silent mutation, where the remaining, c.10718G>C, c.10841G>A, and c.10936G>C, are missense mutations that lead to amino acid alterations from arginine to proline, from serine to asparagine and from aspartic acid to histidine, respectively. According to Majewski and Ott (see, e.g., Majewski and Ott, 2003, Gene, 305: 167-173), arginine, aspartic acid and histidine are the least mutable amino acids with mutability of 0.365, 0.424 and 0.482, respectively. The missense mutation c.10841G>A (serine to asparagine) was associated with neither marbling nor SFD in the reference population, but it impacted the secondary structure of the bovine CRH mRNA significantly (FIGS. 3A-3C). The c.10718G>C (arginine to praline) was significantly associated with SFD, while the c.10936G>C (aspartic acid to histidine) affected both SFD and marbling (Table 2). Therefore, in this case it appears that there is no connection between mRNA secondary structure and phenotype. In addition, three SNPs (g.9657C>T, c.10718G>C and c.10936G>C) had also significant haplotype effects on SFD (FIGS. 4A-4C). Overall, the Example confirmed that CRH is a strong candidate gene that regulates lipid metabolism in mammals. However, the center locations of QTLs on BTA14 detected in different experiments vary for both marbling and SFD (see, e.g., Casas et al., 2000, J Anim Sci. 78: 560-569, Casas et al., 2003, J Anim Sci. 81: 2976-2983 and Mizoshita et al., 2004, J Anim Sci. 82: 3415-3420). This implies that other possible candidate genes on the chromosome might be involved in lipogenesis.

Example 2

Figure 5:
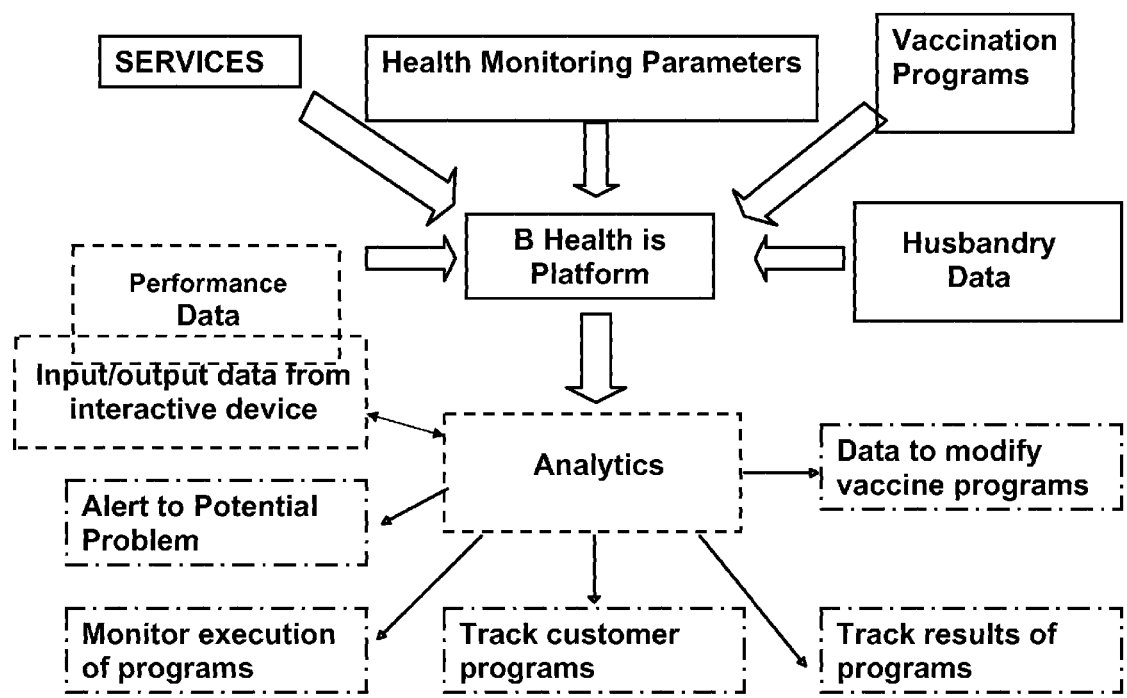
FIG. 5 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

FIG. 5 shows a flowchart of the input of data and the output of results from the analysis and correlation of the data pertaining to the breeding, veterinarian histories and performance requirements of a group of animals such as from bovines. The flowchart illustrated in FIG. 7 further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

Figure 6:
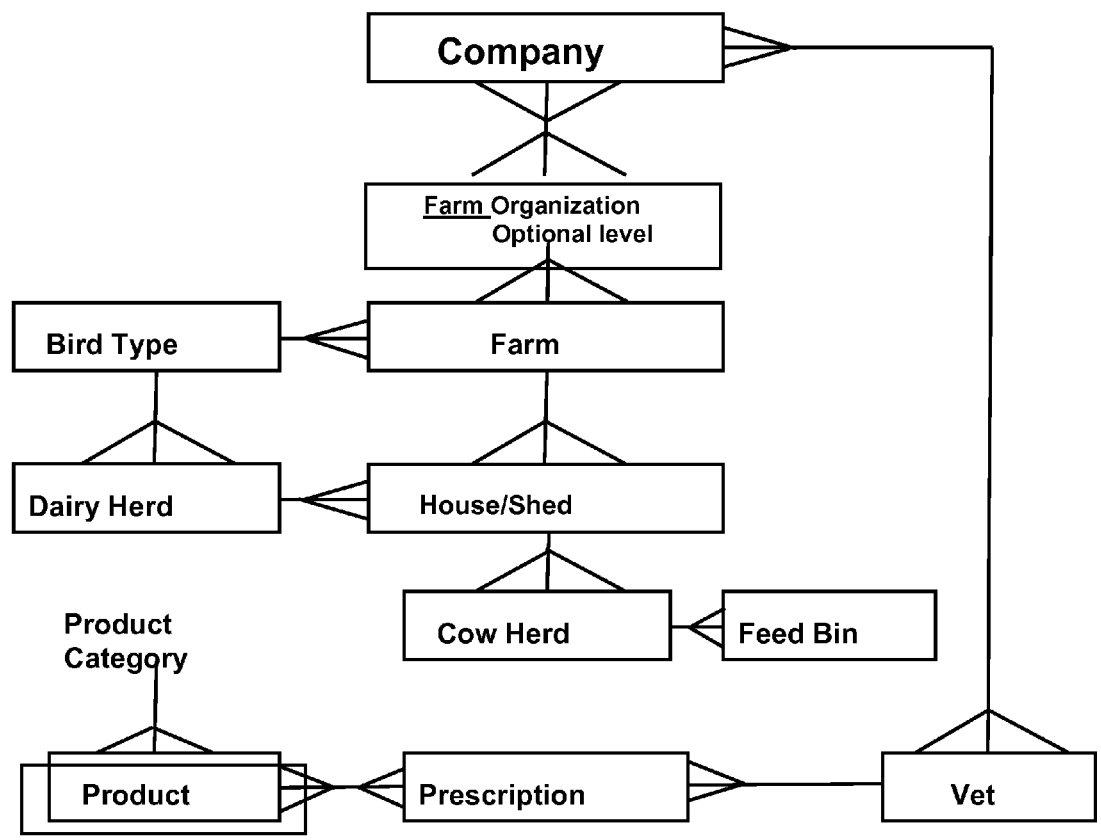
FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 6 illustrates potential relationships between the data elements to be entered into the system. Unidirectional arrows indicate, for example, that a barn is typically owned by only one farm, whereas a farm may own several barns. Similarly, a prescription may include veterinarian products.

Figure 7A:
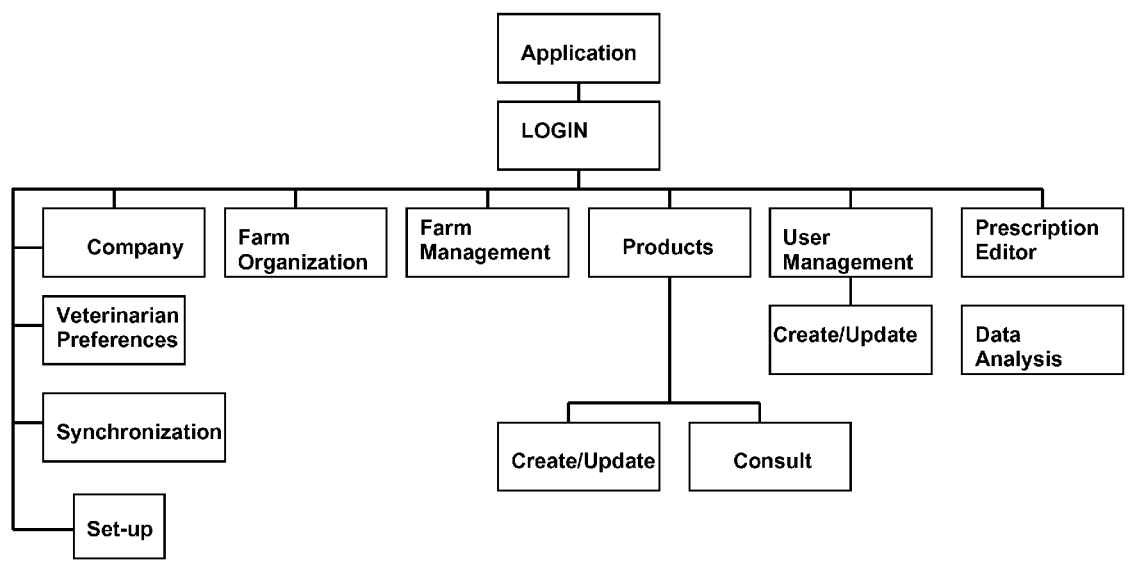
FIG. 7A illustrates the flow of events in the use of the portable computer-based system for data entry on the breeding and rearing of a herd of cows.
Figure 7B:
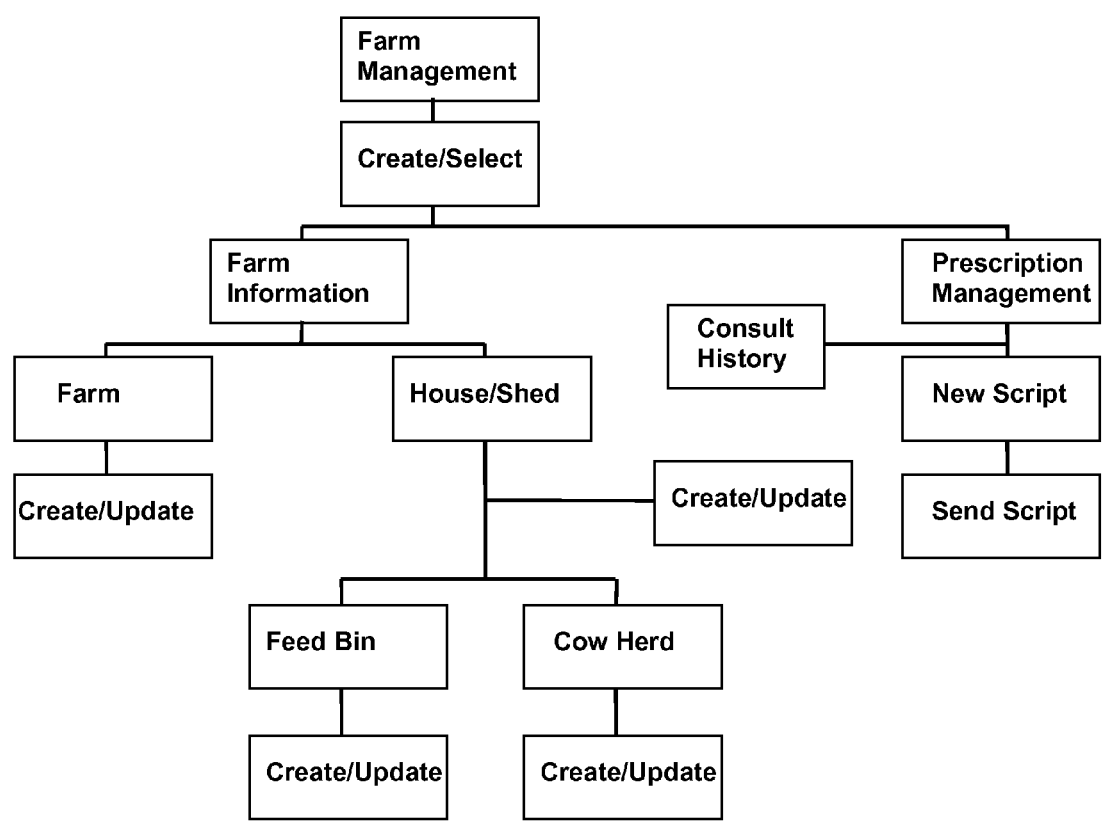
FIG. 7B illustrates the flow of events through the subroutines related to data entry concerning farm management.
Figure 7C:
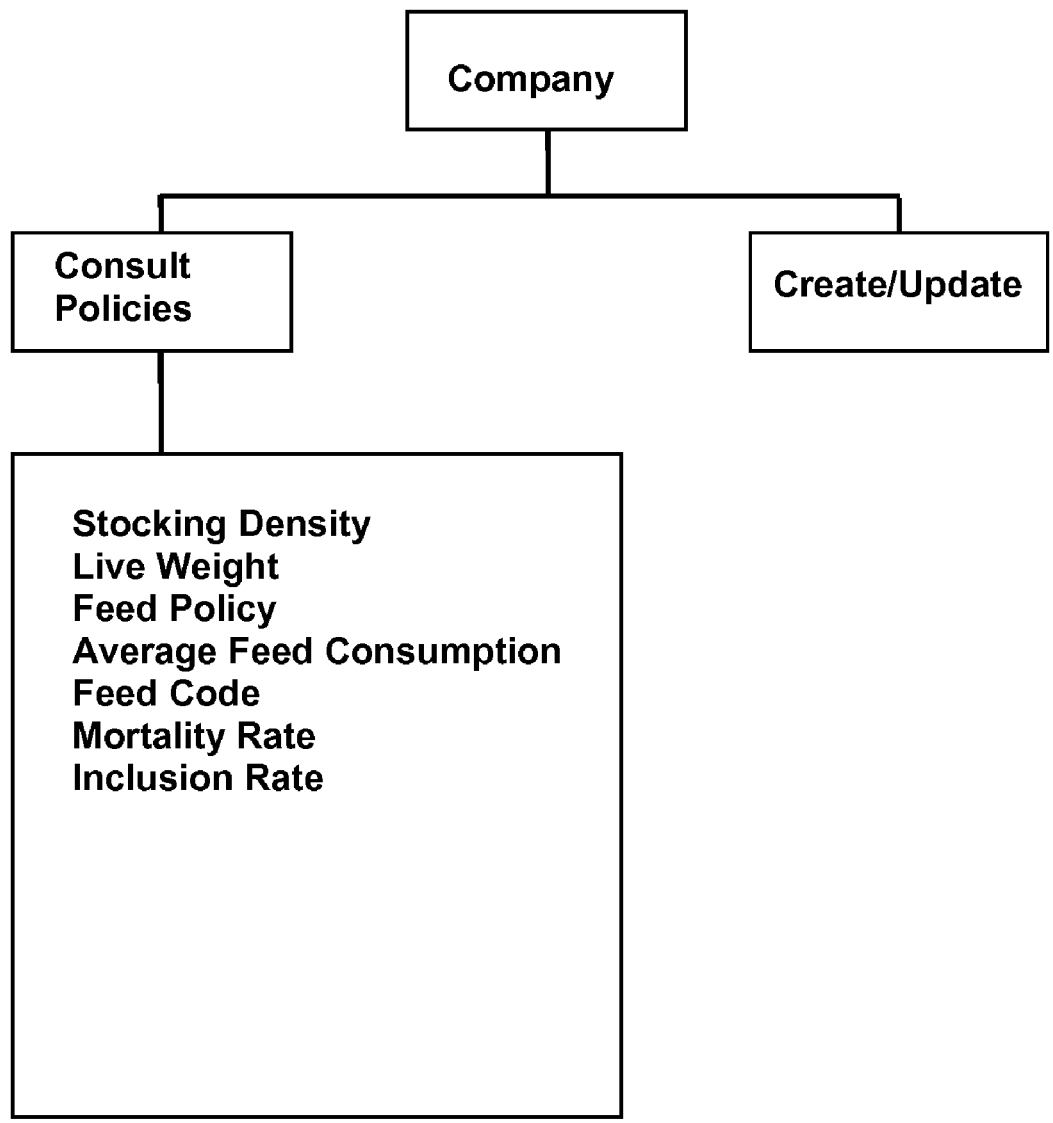
FIG. 7C illustrates the flow of events through the subroutines related to data entry concerning data specific to a company.

FIG. 7A illustrates the flow of events in the use of the portable computer-based system for data entry on the breeding and rearing of a herd of cows. FIG. 7B illustrates the flow of events through the sub-routines related to data entry concerning farm management. FIG. 7C illustrates the flow of events through the sub-routines related to data entry concerning data specific to a company.

Figure 8:
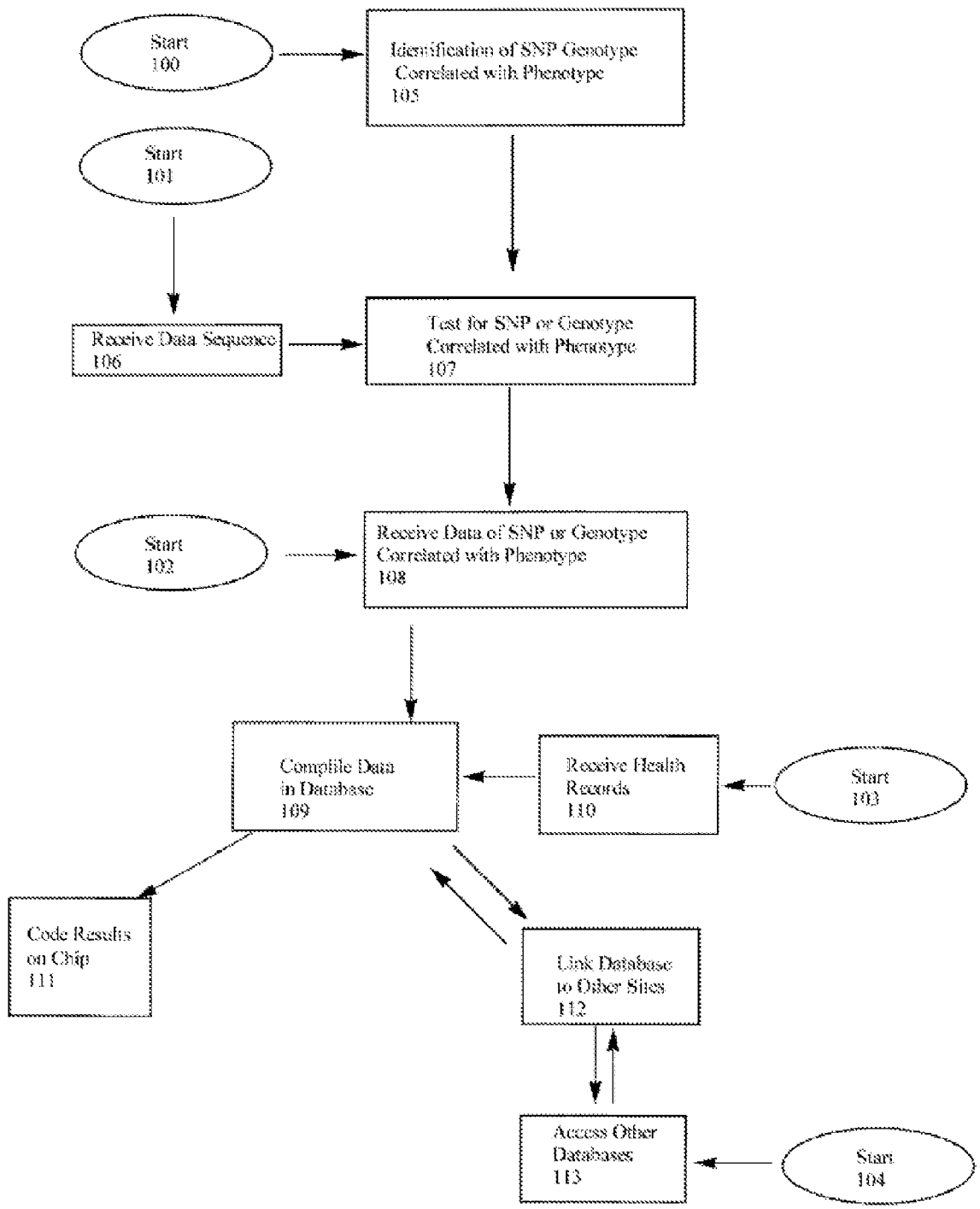
FIG. 8 illustrates a flow chart of the input of data and the output of results from the analysis and the correlation of the data pertaining to the breeding, veterinarian histories, and performance requirements of a group of animals.

FIG. 8 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have a similar polymorphism in a CRH gene comprising:
   (a) determining the genotype of each animal to be sub-grouped by determining the presence of a single nucleotide polymorphism in the CRH gene, and
   (b) segregating individual animals into sub-groups wherein each animal in a sub-group has a similar polymorphism in the CRH gene.

2. A method for sub-grouping animals according to genotype wherein the animals of each sub-group have a similar genotype in the CRH gene comprising:
   (a) determining the genotype of each animal to be sub-grouped by determining the presence of a single nucleotide polymorphism(s) of interest in the CRH gene,
   (b) segregating individual animals into sub-groups depending on whether the animals have, or do not have, the single nucleotide polymorphism(s) in the CRH gene.

3. The method of paragraphs 1 or 2, wherein the single nucleotide polymorphism(s) of interest selected from the group consisting of AAFC03076794.1:g.9657C>T, c.10718G>C, c.10841G>A, c.10893A>C and c.10936G>C.

4. A method for sub-grouping animals according to genotype wherein the animals of each sub-group have a similar genotype in the CRH gene comprising:
   (a) determining the genotype of each animal to be sub-grouped by determining the presence of a single nucleotide polymorphism(s) of interest selected from the group consisting of AAFC03076794.1:g.9657C>T, c.10718G>C, c.10841G>A, c.10893A>C and c.10936G>C, and
   (b) segregating individual animals into sub-groups depending on whether the animals have, or do not have, a single nucleotide polymorphism(s) of interest selected from the group consisting of AAFC03076794.1:g.9657C>T, c.10718G>C, c.10841G>A, c.10893A>C and c.10936G>C.

5. A method for identifying an animal having a desirable phenotype as compared to the general population of animals of that species, comprising determining the presence of a single nucleotide polymorphism in the CRH gene of the animal, wherein the polymorphism is selected from the group consisting of AAFC03076794.1:g.9657C>T, c.10718G>C, c.10841G>A, c.10893A>C and c.10936G>C, wherein the single nucleotide polymorphism is indicative of a desirable phenotype.

6. The method of paragraph 5, wherein the desirable phenotype is marbling and/or subcutaneous fat depth.

7. The method of any one of paragraphs 1 to 6 wherein the animal is a bovine.

8. The method of any one of paragraphs 1 to 7 wherein the CRH gene is a bovine CRH gene.

9. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

10. The method according to paragraph 9, wherein the computer system is an interactive system whereby modifications to the output of the computer-assisted method may be correlated according to the input from the interactive device.

11. The method according to paragraph 9 or 10, further comprising the steps of inputting into the programmed computer diagnostic data related to the health of the cow or herd of cows; and correlating the diagnostic data to the breeding and veterinary histories of the cow or herd of cows.

12. The method according to any one of paragraphs 9 to 11, wherein the veterinary data comprises a vaccination record for a cow or herd of cows.

13. The method according to any one of paragraphs 9 to 12 wherein the health data is selected from the group consisting of husbandry condition data, herd history, and food safety data.

14. The method according to any one of paragraphs 9 to 13, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

15. The method according to any one of paragraphs 9 to 14, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

16. The computer-assisted method according to any one of paragraphs 9 to 15 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

17. A method of transmitting data comprising transmission of information from such methods according to any one of paragraphs 9 to 15, selected from the group consisting of telecommunication, telephone, video conference, mass communication, a presentation, a computer presentation, a POWERPOINT™ presentation, internet, email, and documentary communication.

18. An interactive computer system according to any one of paragraphs 9 to 15 for tracking breeding and welfare histories of cows comprising breeding and veterinarian data corresponding to a bovine or herd of bovines, and wherein the computer system is configured to allow the operator thereof to exchange data with the device or a remote database.

19. The interactive computer system according to paragraph 18, wherein the input and output devices are a personal digital assistant or a pocket computer.

20. A method of doing business for tracking breeding and welfare histories of livestock comprising breeding and veterinarian data corresponding to one or more livestock animals comprising providing to a user the computer system of paragraph 18.

21. A method of doing business for tracking breeding and welfare histories of livestock comprising breeding and veterinarian data corresponding to one or more livestock animals comprising providing to a user the computer system of paragraph 19.

22. The method of doing business according to paragraph 20, further comprising providing the animal owner or customer with sample collection equipment, such as swabs and tags useful for collecting samples from which genetic data may be obtained, and wherein the tags are optionally packaged in a container which is encoded with identifying indicia.

23. The method of doing business according any one of paragraphs 9 to 15, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

24. The method of any one of paragraphs 9 to 24 wherein the data comprises presence or absence of one or more of a single nucleotide polymorphism(s) of interest in the CRH gene.

25. The method of paragraph 24 wherein the single nucleotide polymorphism(s) is selected from the group consisting of AAFC03076794.1:g.9657C>T, c.10718G>C, c.10841G>A, c.10893A>C and c.10936G>C.

26. A method for the diagnosis or monitoring of marbling and/or subcutaneous fat depth in a subject, comprising: obtaining a biological sample from a subject; and determining, using a suitable assay, a presence or absence in the sample of one or more CRH SNPs, as described herein.

27. The method of paragraph 26, wherein the subject is bovine.

28. A method for marker-assisted selection to improve marbling and/or subcutaneous fat depth, comprising screening, as part of a selection scheme, based on one or more CRH SNPs, as described herein, to enhance selection for marbling and/or subcutaneous fat depth.

30. The method of paragraph 29, wherein selecting is to and reduce marbling and/or subcutaneous fat depth.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a thicker or thinner subcutaneous fat depth (SFD), as compared to the general population of bovine animals, said method comprising:
   (a) obtaining a biological sample from a bovine, said sample comprising nucleic acids from said bovine including the bovine corticotropin-releasing hormone (CRH) gene;
   (b) detecting in said nucleic acids:
      (i) a C in both alleles of the CRH gene at a position corresponding to position 285 of SEQ ID NO: 2; or
      (ii) a T in at least one allele of the CRH gene at a position corresponding to position 285 of SEQ ID NO: 2; and
   (c) correlating a C in both alleles of the CRH gene at a position corresponding to position 285 of SEQ ID NO: 2 with a thinner SFD phenotype as compared to the general population of bovines, or a T in at least one allele of the CRH gene at a position corresponding to position 285 of SEQ ID NO: 2 with a thicker SFD phenotype as compared to the general population of bovine animals.

2. The method of claim 1 further comprising sub-grouping animals according to genotype, wherein the animals of each sub-group have the same polymorphism in the CRH gene, said method comprising:
   (a) determining the genotype of each animal to be sub-grouped by determining the presence of a single nucleotide polymorphism in the CRH gene according to the method of claim 1, and
   (b) segregating individual animals into sub-groups depending on whether the animals have, or do not have, the single nucleotide polymorphisms in the CRH gene.

* * * * *

SEQUENCE LISTING

<160> NUMBER OF SEQ ID NOS: 18

<210> SEQ ID NO 1
<211> LENGTH: 745
<212> TYPE: DNA
<213> ORGANISM: Bos taurus

<400> SEQUENCE: 1

| | | | | | | |
|---|---|---|---|---|---|---|
| cacgcgtccg | ggaagagaag | aggaaaagaa | cagagtggga | agagaaagga | gaagggaaga | 60 |
| gaaccgctga | aaaaaaagcc | ccagagactt | tctctgcaga | gaagcgctgc | gccccgctca | 120 |
| cctgcagaag | cacctcggaa | gcgcccgcta | aaatgcgact | gcggctgctc | gtgtccgtgg | 180 |
| gcgtcctgct | ggtggctctg | ctgccctccc | cgccatgcag | ggcctcctc | agccggggc | 240 |
| ccatcccggg | tgcccggcag | gcatcacagc | accccagcc | cctgagtttc | ttccagccgc | 300 |
| cgccgcagcc | ccaggaaccc | caggctctgc | ccaccctact | ccgtgttggg | gaggaatact | 360 |
| tcctccgcct | gggtaaccte | gatgagaccc | gggctgctcc | gctctctccc | gccgcctcgc | 420 |
| ctctcgccag | cagaagcagc | agtcgccttt | tccggacaa | ggtggccgcc | aacttttcc | 480 |
| gagcgctgct | gcagccccgg | cgcccattcg | acagcccagc | gggtcccgcg | aacgcggca | 540 |
| cggagaacgc | cctcggcagc | cgccaggagg | cgccggccgc | caggaagagg | cgatcccagg | 600 |
| aacctcccat | ctccctggat | ctcaccttcc | acctcctccg | agaagtcttg | gaaatgacca | 660 |
| aggccgatca | gttagcacag | caagctcata | acaacaggaa | actgttggac | attgctggga | 720 |
| aatgaaacgg | tgcgtttggc | taaaa | | | | 745 |

<210> SEQ ID NO 2
<211> LENGTH: 2059
<212> TYPE: DNA
<213> ORGANISM: Bos taurus

<400> SEQUENCE: 2

| | | | | | | |
|---|---|---|---|---|---|---|
| cttccccttc | tctcccctcc | cattcactct | cttttctgac | cttcccttg | gccttcccta | 60 |
| gtaagaggcc | agtatgtttt | cacacttggg | aaatctcatt | caagaatttt | tgtcaatgga | 120 |
| caagtcataa | gaagcccttc | cattttaggg | ctcgttgacg | tcatcaagga | ggcgataaat | 180 |
| atctgttgat | ataattggat | gtgagattca | gtgttgagat | agcaaaaatt | ctgcccctcg | 240 |
| ttcccgggca | gggccctatg | atttatgcag | gagcagaggc | agcgcgcaat | ccagctgtca | 300 |
| agagagcgtc | agcttattag | gcaaatgctg | cgtggtttct | gaagagggtc | gacactataa | 360 |
| aatcccttc | caggctctgg | tgtggagaaa | ctcagagccc | acgtccgtgg | agagacagaa | 420 |
| gaggaagaga | agaggaaaag | aacagagtgg | gaagagaaag | gagaagggaa | gagaaccgct | 480 |
| gaaaaaaaag | ccccagagac | tttctctgca | gagaagcgct | gcgccccgct | cacctgcaga | 540 |
| agcacctcgg | aaggtaggga | gcgcctagac | agaactgcgc | ctccagcttt | gcactgcctg | 600 |
| agctgccagg | gtgtgcgcag | cgctgccggc | tgttcctagg | cgtgtgtgta | tatgtgtgtg | 660 |
| tgtgtttgtg | tgtgaacgcg | cgcgcgtggg | cgcgcgtttg | tgcgcgcccg | tgccacaaga | 720 |
| ttccaataga | tagtagctga | gatgctacta | aaagcaaact | tagacggctg | ctcagcgtta | 780 |
| cctgaactgg | ccgttaatcc | tcgctgtgta | acgagcccc | catccatccc | gaccaccacc | 840 |
| gagagaaccg | agggcaggga | tgggaaaaga | ggaaggagag | gcagcagttc | tgtttggagg | 900 |
| aaaagctgaa | acatccggaa | agggtggtgg | tgggtcgcg | gggagggggg | aatgtttaga | 960 |
| gcccttgaga | ccacgaattt | gcaggtcttc | tttagagccc | ggggaattga | tctgggggaa | 1020 |

```
tcgttagaca ggggactcgg ggaccctccc taagtgagtc ttgtaaggag agtcgctcca   1080
gcctggagcg ggactgagcc ttgttgctgc gccctgccct tccaagctgc tccccttggt   1140
ctcactccat ctctggaagt cctaattcgg gcgcttcagc actacggaca gcgccccacc   1200
cgcgccggga gctgggtctg tgggtgtcgt cctgcgggaa gactcccagt ggagctcaac   1260
tctgataact ctctctttt ttctctctca ttccgccccc tgcccacctc tgtaccgcaa   1320
ttagcgcccg ctaaaatgcg actgcggctg ctcgtgtccg tgggcgtcct gctggtggct   1380
ctgctgccct ccccgccatg cagggccctc tcagccgggg gcccatccc gggtgcccgg   1440 caggcatcac agcacccccc gccctgagt tcttccagc cgccgccgca gccccaggaa    1500
ccccaggctc tgcccaccct actccgtgtt ggggaggaat acttcctccg cctgggtaac   1560
ctcgatgaga cccgggctgc tccgctctct cccgccgcct cgcctctcgc cagcagaagc   1620
agcagtcgcc tttctccgga caaggtggcc gccaactttt tccgagcgct gctgcagccc   1680
cggcgcccat tcgacagccc agcgggtccc gcggaacgcg gcacggagaa cgccctcggc   1740
agccgccagg aggcgccggc cgccaggaag aggcgatccc aggaacctcc catctccctg   1800
gatctcacct tccacctcct ccgagaagtc ttggaaatga ccaaggccga tcagttagca   1860
cagcaagctc ataacaacag gaaactgttg gacattgctg ggaaatgaaa cggtgcgttt   1920
ggctaaaaag attctgtatt tagcacaaaa gtgaatttaa aaatctaaaa attgaaaaat   1980
aaaaatacaa tattctatac catagcattg ctctgatacc atgttttattt ttatatagat   2040 tgagatgtag aggatgtac                                                2059

<210> SEQ ID NO 3
<211> LENGTH: 66
<212> TYPE: DNA
<213> ORGANISM: Bos taurus

<400> SEQUENCE: 3
ggcagggccc tatgatttat gcaggagcag aggcagcgcg caatccagct gtcaagagag    60
cgtcag                                                               66

<210> SEQ ID NO 4
<211> LENGTH: 66
<212> TYPE: DNA
<213> ORGANISM: Bos taurus

<400> SEQUENCE: 4
ggcagggccc tatgatttat gcaggagcag aggcagcgtg caatccagct gtcaagagag    60
cgtcag                                                               66

<210> SEQ ID NO 5
<211> LENGTH: 66
<212> TYPE: DNA
<213> ORGANISM: Homo sapiens

<400> SEQUENCE: 5
ggcagggccc tatgatttat gcaggagcag aggcagcacg caatcgagct gtcaagagag    60
cgtcag                                                               66

<210> SEQ ID NO 6
<211> LENGTH: 66
<212> TYPE: DNA
<213> ORGANISM: Pan troglodytes
```

-continued

```
<400> SEQUENCE: 6
ggcagggccc tatgatttat gcaggagcag aggcagcacg caatcgagct gtcaagagag    60
cgtcag                                                               66

<210> SEQ ID NO 7
<211> LENGTH: 66
<212> TYPE: DNA
<213> ORGANISM: Sus scrofa

<400> SEQUENCE: 7
ggcagggccc tatgatttat gcaggagcag aggcagcacg caatcgagct gtcaagagag    60
cgtcag                                                               66

<210> SEQ ID NO 8
<211> LENGTH: 66
<212> TYPE: DNA
<213> ORGANISM: Macaca sp.

<400> SEQUENCE: 8
ggcagggccc tatgatttat gcaggagcag aggcagcacg caatcgagct gtcaagagag    60
cgtcag                                                               66

<210> SEQ ID NO 9
<211> LENGTH: 66
<212> TYPE: DNA
<213> ORGANISM: Canis sp.

<400> SEQUENCE: 9
ggcagggccc tatgatttct gcaggagcag aggcagcacg caatcgagct gtcaagagag    60
cgtcag                                                               66

<210> SEQ ID NO 10
<211> LENGTH: 66
<212> TYPE: DNA
<213> ORGANISM: Mus musculus

<400> SEQUENCE: 10
ggcagggccc tattatttat gcaggagcag aggcagcacg caatcgagct gtcaagagag    60
cgtcag                                                               66

<210> SEQ ID NO 11
<211> LENGTH: 66
<212> TYPE: DNA
<213> ORGANISM: Rattus sp.

<400> SEQUENCE: 11
ggcagggccc tattatttat gcaggagcag aggcagcacg caatcgagct gtcaagagag    60
cgtcag                                                               66

<210> SEQ ID NO 12
<211> LENGTH: 63
<212> TYPE: DNA
<213> ORGANISM: Ovis sp.

<400> SEQUENCE: 12
ggcaggccta tgatttatgc aggagcagag gcagcggcaa tccagctgtc aagagagcgt    60
cag                                                                  63
```

```
<210> SEQ ID NO 13
<211> LENGTH: 66
<212> TYPE: DNA
<213> ORGANISM: Artificial Sequence
<220> FEATURE:
<223> OTHER INFORMATION: Description of Artificial Sequence: Synthetic
      consensus nucleotide

<400> SEQUENCE: 13
ggcagggccc tatgatttat gcaggagcag aggcagcgcg caatccagct gtcaagagag      60
cgtcag                                                                 66

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cccctcccat tcactctctt ttct                                             24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agttctgtct aggcgctccc tacc                                             24

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gggtctgtgg gtgtcgtcct                                                  20

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaaaataaac atggtatcag agcaatg                                          27

<210> SEQ ID NO 18
<211> LENGTH: 540
<212> TYPE: DNA
<213> ORGANISM: Bos taurus

<400> SEQUENCE: 18
cccctcccat tcactctctt ttctgacctt ccctttggcc tttcctagta agaggccagt      60
atgttttcac acttgggaaa tctcattcaa gaattttgt caatggacaa gtcataagaa      120
gcccttccat tttagggctc gttgacgtca tcaaggaggc gataaatatc tgttgatata     180
```

```
attggatgtg agattcagtg ttgagatagc aaaaattctg cccctcgttc ccgggcaggg    240
ccctatgatt tatgcaggag cagaggcagc gygcaatcca gctgtcaaga gagcgtcagc    300
ttattaggca aatgctgcgt ggtttctgaa gagggtcgac actataaaat cccattccag    360
gctctggtgt ggagaaactc agagcccacg tccgtggaga gacagaagag gaagagaaga    420
ggaaaagaac agagtgggaa gagaaaggag aagggaagag aaccgctgaa aaaaaagccc    480
cagagacttt ctctgcagag aagcgctgcg ccccgctcac ctgcagaagc acctcggaag    540
```